United States Patent [19]

Eberlein et al.

[11] Patent Number: 5,001,122
[45] Date of Patent: Mar. 19, 1991

[54] USE OF DIAZEPINONES FOR TREATING DISORDERS OF THE MICROCIRCULATION

[75] Inventors: Wolfgang Eberlein; Volker Trach; Wolfhard Engel; Gerhard Mihm; Norbert Mayer, all of Biberach; Henri Doods, Warthausen; Richard Reichl, Gau-Algesheimn, all of Fed. Rep. of Germany

[73] Assignee: Dr. Karl Thomae GmbH, Biberach an der Riss, Fed. Rep. of Germany

[21] Appl. No.: 353,262

[22] Filed: May 17, 1989

[30] Foreign Application Priority Data

May 17, 1988 [DE] Fed. Rep. of Germany ....... 3816709

[51] Int. Cl.$^5$ ............................................. A61K 31/55
[52] U.S. Cl. ..................................... 514/220; 514/921
[58] Field of Search ........................................ 514/220

[56] References Cited

FOREIGN PATENT DOCUMENTS 3611097 10/1987 Fed. Rep. of Germany .

OTHER PUBLICATIONS

*Chemical Abstracts*, 106:156503j (1987).

*Primary Examiner*—Stanley J. Friedman
*Assistant Examiner*—Terry Wilson
*Attorney, Agent, or Firm*—David E. Frankhouser; Daniel Reitenbach; Mary-Ellen M. Timers

[57] ABSTRACT

A method for treating shock in a patient, which comprises administering to the patient a therapeutically effective amount of a diazepinone of the general formula:

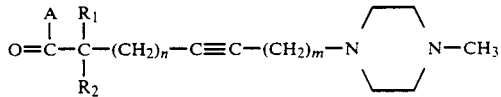

wherein

A represents a 5,11-dihydro-6H-pyrido[2,3-b] [1,4] benzodiazepin-6-one group bound in the 11-position; a 5,10-dihydro-11H-dibenzo [b,e] [1,4] diazepin-11-one group bound in the 5-position; a 5,11-dihydro-10H-pyrido [3-2b] [1-4] benzodiazepin-10-one group bound in the 5-position; a 4,9-dihydro-10H-thieno [3,4-b] [1,5] benzodiazpin-10-one group bound in the 4-position, unsubstituted or substituted at the 1- or 3-position or both in the 1- and 3-position by an alkyl group having from 1 to 4 carbon atoms, or in the 3-positionby chlorine, fluorine or bromine; a 6-11-dihydro-5H-pyrido [2,3-b] [1,5] benzodiazepin-5-one group bound in the 11-position; or a 1-methyl-1,4,9,10-tetrahydropyrrolo-[3,2-b] [1,5] benzodiazepin-10-one group bound in the 4-position, unsubstituted or substituted at the 3-position by methyl or methyl or chlorine;

$R_1$ represents a hydrogen atom or an alkyl group having from 1 to 3 carbon atoms;

$R_2$ represents an alkyl group having from 1 to 3 carbon atoms; and n and m each represent an integer from 1 to 3.

8 Claims, No Drawings

USE OF DIAZEPINONES FOR TREATING DISORDERS OF THE MICROCIRCULATION

The invention relates to the use of diazepinones of general formula I

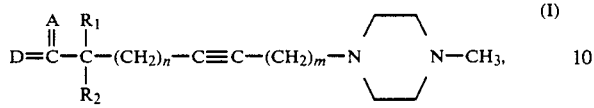

wherein

A represents the 5,11-dihydro-6H-pyrido[2,3-b][1,4]-benzodiazepin-6-one group bound in the 11-position, the 5,10-dihydro-11H-dibenzo[b,e][1,4]diazepin-11-one group bound in the 5-position, the 5,11-dihydro-10H-pyrido[3,2-b][1,4]benzodiazepin-10-one group bound in the 5-position, the 4,9-dihydro-10H-thieno[3,4-b][1,5]benzodiazepin-10-one group bound in the 4-position, which may be substituted in the 1- and/or 3-positions by alkyl groups having 1 to 4 carbon atoms or in the 3-position by chlorine, fluorine or bromine, the 6,11 dihydro-5H-pyrido[2,3-b][1,5]benzodiazepin-5-one group bound in the 11-position or the 1-methyl-1,4,9,10-tetrahydropyrrolo[3,2-b][1,5]benzodiazepin-10-one group bound in the 4-position, which may be substituted in the 3-position by methyl or chlorine, $R_1$ represents a hydrogen atom or an alkyl group having 1 to 3 carbon atoms, $R_2$ represents an alkyl group having 1 to 3 carbon atoms, and n and m independently of each other represent the integers 1 to 3, and the acid addition salts thereof for the treatment of disorders of the microcirculation, for example for the treatment of haemorrhagic shock and peripheral blood flow disorders of various origins.

Condensed diazepinones with the properties of inhibiting ulcer formation and the secretion of gastric acid are already known from EP-A-0 039 519 and 0 057 428 and from U.S. Pat. Nos. 3,660,380; 3,691,159; 4,213,984; 4,213,985; 4,210,648; 4,410,527; 4,424,225; 4,424,222 and 4,424,226.

From DE-A1-3 611 097 it is known that the compound 5,11-dihydro-11-[1-oxo-2-methyl-6-(4-methyl-1-piperazinyl)-4-hexynyl]-6H-pyrido[2,3-b][1,4]benzodiazepin-6-one, which falls within general formula I above, and the acid addition salts thereof have an antithrombotic effect. The compound, its production and processing into pharmaceutical preparations are described in this Offenlegungsschrift. The other compounds of general formula I above may be prepared analogously to the method described in DE-A1-3 523 002.

Surprisingly, it has now been found that the compounds of general formula I, particularly those wherein A represents the 5,11-dihydro-6H-pyrido[2,3-b][1,4]benzodiazepin-6-one group, $R_1$ represents a hydrogen atom and $R_2$ represents the methyl group, but especially 5,11-dihydro-11-[1-oxo-2-methyl-6-(4-methyl-1-piperazinyl)-4-hexynyl]-6H-pyrido[2,3-b][1,4]benzodiazepin-6-one, the enantiomers and isomers (cf. DE-A-3 626 095) of these compounds and the physiologically acceptable acid addition salts thereof are particularly suitable for the treatment of disorders of the microcirculation. Examples of microcirculatory disorders treatable by the diazepinones of the present invention include:

(1) shock, e.g., haemorrhagic shock, endotoxin shock, traumatic shock, and the like;
(2) ischaemic conditions other than shock, such as cerebral ischaemia, intestinal ischaemia, myocardial ischaemia, and the like; and
(3) peripheral blood flow disorders such as: (a) peripheral vascular diseases such as ischaemic limb (e.g. intermittent claudication) and vasospastic disorders (e.g. Raynaud's Syndrome); (b) microangiopathy, e.g. myocardial microangiopathy, retinopathy, nephropathy in diabetes, thromboangiitis obliterans; and the like. The active substance has only an extremely low affinity for muscarinic receptors and consequently no undesirable atropine-like side effects occur at therapeutic doses.

Hitherto, there has been no causal therapy available for shock and other microcirculatory disorders; up till now, these syndromes have been treated purely symptomatically, e.g.

in the case of shock: by means of Dextran 40 infusions, glucocorticoids, adrenalin-bolus, aprotinin and dobutamine (for maintaining kidney function), in the case of microcirculatory disorders: by administering, for example, rutin, papaverin and occasionally alpha-blockers or $Ca^{2+}$-antagonists.

The above-mentioned syndromes have also been treated with nonselective antimuscarinics, e.g. atropine, N-butylscopolammonium bromide, tropine benzylate, glycopyrronium bromide, oxybutynin, and myotropic spasmolytics, e.g. papaverin, moxaverin, frequently combined with other active substances. However, all these substances have major side effects (e.g. on the heart or on the function of the salivary glands). By contrast, the substances on which the invention is based are extremely weak antimuscarinic agents and in therapeutic doses there are no atropine-like side effects.

The substances of general formula I, particularly 5,11-dihydro-11-[1-oxo-2-methyl-6-(4-methyl-1-piperazinyl)-4-hexynyl]-6H-pyrido[2,3-b][1,4]benzodiazepin-6-one and the salts thereof, by contrast, provide a starting point for the causal treatment of shock and microcirculatory disorders for the first time.

The suitability of 5,11-dihydro-11-[1-oxo-2-methyl-6-(4-methyl-1-piperazinyl)-4-hexynyl]-6H-pyrido[2,3-b]-[1,4]benzodiazepin-6-one dihydrochloride for use in shock therapy according to the invention was confirmed in animal trials on a Cremaster model. This model is an established method (S. Hergenröder "Microcirculation in Haemorrhagic Shock", Diploma Thesis in the Biology Department of Joh.-Gutenberg University, Mainz 1987). This model was used to determine effects on systemic blood pressure, heart rate, the shock index calculated from them and important microcirculatory parameters such as the diameter of the arterioles, the erythrocyte flow rate and the microperfusion (organ blood flow) calculated therefrom and the survival rate. The procedure consists of a preparatory control phase followed by spontaneous bleeding with a rapid fall in blood pressure to 25 mmHg, an isovolumic intravenous 10 minute infusion with physiological NaCl solution (control animals) or physiological NaCl solution with the active substances dissolved therein followed by a final observation phase (60 to 120 minutes). The second model is distinguished by a two-day observation phase without preparation of the Cremaster model.

The end of the bleeding phase is characterised by a stopflow in the intravitally observed microcircular area, caused by the drastic blood loss and the sharp fall in blood pressure which this involves.

The haemodynamic effects in the control group treated with physiological NaCl solution were slight and of short duration only, with a survival rate of only 4 out of 20 animals after 60 minutes and no animals surviving after 120 minutes. In the group (N=7) treated with 5,11-dihydro-11-[1-oxo-2-methyl-6-(4-methyl-1-piperazinyl)-4-hexynyl]-6H-pyrido[2,3-b][1,4]benzodiazepin-6-one dihydrochloride (2 mg/kg), on the other hand, a recovery of the systemic, particularly the microcirculatory, parameters was observed. A survival rate of 86% was achieved.

In the second "shock model" the survival rate is comparable with the group treated with the compound proposed according to the invention, whereas in the nonpretreated group 3 out of 15 animals survived, 13 out of 15 animals survived in the group pretreated with the active substance.

CHbb/Thom rats weighing from 100 to 120 g were used for the investigation; they were anaesthetised with urethane (120 mg/100 g of rat). 2.0 mg/kg of active substance were administered intravenously in the form of the dihydrochloride.

As systemic parameters, the blood pressure (systolic and diastolic) and the heart rate were measured and as microcirculatory parameters the blood vessel diameter and the erythrocyte flow rate were measured and from them the shock index (=heart rate/systolic blood pressure) and the microflow (from the blood vessel diameter and erythrocyte flow rate) were calculated.

The values found or calculated are shown in FIGS. 1 to 7; the active substance according to the present invention mentioned hereinbefore is referred to as Substance A for short. The confidence limits are also given for the individual measured points.

For the shock index, FIG. 1 gives, for Substance A, a very uniform curve close to the base line over the entire test period, indicating a significant improvement in the management of shock, compared with the control. FIG. 4 shows that the microflow, i.e. the organ perfusion, is continuously raised by Substance A from the 60th minute onwards. FIG. 7 gives the percentage survival rate over the observation period of 2 hours. Only 1 out of 7 animals died, corresponding to a survival rate of 86%. Not one animal survived of the control animals.

The following Table shows the percentage of animals surviving in both test series after 2 hours and after 48 hours:

TABLE

| Observation period | Percentaoe of survivors | | | |
|---|---|---|---|---|
| | 1st Test Series | | 2nd Test Series | |
| | 2 h | | 48 h | |
| Control | N = 20 | 0% | N = 10 | 20% |
| Substance A | N = 7 | 86% | N = 10 | 80% |

In the light of the pharmacological findings, the compounds of general formula I and the pharmacologically acceptable acid addition salts thereof are particularly suitable for the causal treatment of states of shock and for use in shock therapy.

For the treatment of acute shock the compounds may be administered intravenously—as a bolus injection or as an infusion and for the general treatment of blood flow disorders they may also be administered orally, e.g. in the form of plain or coated tablets.

The therapeutically effective dosage range is between 0.02 and 10 mg/kg of body weight. The active substances or the physiologically acceptable salts thereof may be incorporated in conventional pharmaceutical preparation forms, e.g. solutions, suppositories, plain or coated tablets, capsules or infusions. The single dose is generally between 0.002 and 5 mg/kg, preferably 0.05 and 1.0 mg/kg, of body weight, optionally administered in the form of several individual doses to achieve the desired therapeutic effect.

The active substances may also be converted into the physiologically acceptable salts thereof using corresponding inorganic or organic acids. Examples of acids which have proved particularly suitable are hydrochloric, hydrobromic, sulphuric, methylsulphuric, phosphoric, tartaric, fumaric, citric, maleic, succinic and malic acid.

The following Examples illustrate the preparation of some pharmaceutical administration forms:

EXAMPLE I

Tablets containing 50 mg of 5,11-dihydro-11-[1-oxo-2-methyl-6-(4-methyl-1-piperazinyl)-4-hexynyl]-6H-pyrido-[2,3-b][1,4]benzodiazepin-6-one

| Composition: tablet contains: | |
|---|---|
| Active substance | 50.0 mg |
| Lactose | 148.0 mg |
| potato starch | 65.0 mg |
| Magnesium stearate | 2.0 mg |
| | 265.0 mg |

Method of Preparation

A 10% mucilage is prepared from potato starch by heating. The active substance, lactose and remaining potato starch are mixed together and granulated with the above mucilage through a 1.5 mm mesh screen. The granules are dried at 45° C., rubbed through the same screen again, mixed with magnesium stearate and compressed to form tablets.

| Weight of tablet: | 220 mg |
|---|---|
| Punch: | 9 mm |

EXAMPLE II

Coated tablets containing 50 mg of 5,11-dihydro-11-[1-oxo-2-methyl-6-(4-methyl-1-piperazinyl)-4-hexynyl]-6H-pyrido[2,3-b][1,4]benzodiazepin-6-one The tablets prepared according to Example I are coated, by a known method, with a coating consisting essentially of sugar and talc. The finished coated tablets are polished with beeswax.

Weight of coated tablet: 300 mg

EXAMPLE III

Ampoules containing 10 mg of 5,11-dihydro-11-[1-oxo-2-methyl-6-(4-methyl-1-piperazinyl)-4-hexynyl]-6H-pyrido[2,3-b][1,4]benzodiazepin-6-one-dihydrochloride

| Composition: ampoule contains: | |
|---|---|
| Active substance | 10.0 mg |
| Sodium chloride | 8.0 mg |
| Distilled water ad | 1 ml |

Method of Preparation

The active substance and sodium chloride are dissolved in distilled water and then made up to the volume specified. The solution is sterile filtered and transferred into 1 ml ampoules.

Sterilisation: 20 minutes at 120° C.

EXAMPLE IV

Suppositories containing 50 mg of 5,11-dihydro-11-[1-oxo-2-methyl-6-(4-methyl-1-piperazinyl)-4-hexynyl]-6H-pyrido[2,3-b][1,4]benzodiazepin-6-one

| Composition: 1 suppository contains: | |
|---|---|
| Active substance | 50.0 mg |
| Suppository mass (e.g. Witepsol W 45 ®) | 1 695.0 mg |
| | 1 745.0 mg |

Method of Preparation

The finely powdered active substance is suspended in the molten suppository mass which has been cooled to 40° C. The mass is poured at 37° C. into slightly chilled suppository moulds.

Weight of suppository 1.745 g.

EXAMPLE V

Drops containing 5,11-dihydro-11-[1-oxo-2-methyl-6-(4-methyl-1-piperazinyl)-4-hexynyl]-6H-pyrido[2,3-b][1,4]-benzodiazepin-6-one dihydrochloride

| Composition: 100 ml of drops solution contain: | |
|---|---|
| Methyl p-hydroxybenzoate | 0.035 g |
| Propyl p-hydroxybenzoate | 0.015 g |
| Aniseed oil | 0.05 g |
| Menthol | 0.06 g |
| Pure ethanol | 10.0 g |
| Active substance | 5.0 g |
| Sodium cyclamate | 1.0 g |
| Glycerol | 15.0 g |
| Distilled water ad | 100.0 ml |

Method of Preparation

The active substance and sodium cyclamate are dissolved in about 70 ml of water and glycerol is added. The p-hydroxybenzoates, aniseed oil and menthol are dissolved in ethanol and this solution is added with stirring to the aqueous solution. Finally, the solution is made up to 100 ml with water and filtered to remove any suspended particles.

We claim:

1. A method for treating shock in a patient, which comprises administering to the patient a therapeutically effective amount of a diazepinone of the general formula:

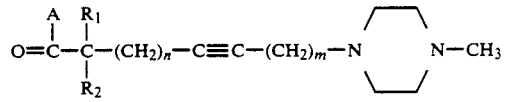

wherein

A represents a 5,11-dihydro-6H-pyrido[2,3,-b][1,4]-benzodiazepin-6-one group bound in the 11-position; a 5,10-dihydro-11H-dibenzo [b,e][1,4] diazepin-11-one group bound in the 5-position; a 5,11-dihydro-10H-pyrido [3,2-b][1,4]benzodiazepin-10-one group bound in the 5-position; a 4,9-dihydro-10H-thieno [3,4-b][1,5]benzodiazepin-10-group bound in the 4-position, unsubstituted or substituted at the 1- or 3-position or in both the 1- and 3-position by an alkyl group having from 1 to 4 carbon atoms, or in the 3-position by chlorine, fluorine or bromine; a 6,11-dihydro-5H-pyrido [2,3-b][1,5]benzodiazepin-5-one group bound in the 11-position; or a 1-methyl-1,4,9,10-tetrahydropyrrolo-[3,2-b][1,5]benzodiazepin-10-one group bound in the 4-position by methyl or chlorine;

$R_1$ represents a hydrogen atom or an alkyl group having from 1 to 3 carbon atoms;

$R_2$ represents an alkyl group having from 1 to 3 carbon atoms; and n and m represent an integer from 1 to 3.

2. The method of claim 1 wherein A is 5,11-dihydro-6H-pyrido [2,3-b][1,4]benzodiazepin-6-one.

3. The method of claim 2 wherein $R_1$ is hydrogen and $R_2$ is methyl.

4. The method of claim 3 wherein the diazepinone is 5,11-dihydro-11-[1-oxo-2-methyl-6-(4-methyl-1-piperazinyl)-4-hexynyl]-6H-pyrido [2,3-b][1,4]benzodiazepin-6-one.

5. A method for treating shock in a patient, which comprises administering to the patient a therapeutically effective amount of a pharmaceutical composition comprising a diazepinone of the formula:

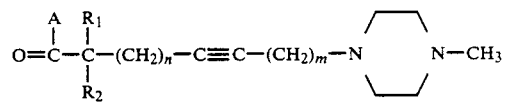

wherein

A represents a 5,11-dihydro-6H-pyrido[2,3-b][1,4]-benzodiazepin-6-one group bound in the 11-position; a 5,10-dihydro-11H-dibenzo [b,e][1,4]diazepin-11-one group bound in the 5-position; a 5,11-dihydro-10H-pyrido[3,2-b][1,4]benzodiazepin-10-one group bound in the 5-position; a 4,9-dihydro-10H-thieno [3,4-b][1,5]benzodiazepin-10-one group bound in the 4-position, unsubstituted or substituted at the 1- or 3-position or in both the 1- and 3-position by an alkyl group having from 1 to 4 carbon atoms, or in the 3-position by chlorine, fluorine or bromine; a 6,11-dihydro-5H-pyrido [2,3-b][1,5]benzodiazepin-5-one group bound in the 11-position; or a 1-methyl-1,4,9,10-tetrahydropyrrolo-[3,2-b][1,5]benzodiazepin-10-group bound in the 4-position by methyl or chlorine;

$R_1$ represents a hydrogen atom or an alkyl group having from 1 to 3 carbon atoms;

R2 represents an alkyl group having from 1 to 3 carbon atoms; and n and m each represent an integer from 1 to 3.

6. The method of claim 5 wherein A is 5,11-dihydro-6H-pyrido [2,3-b][1,4]benzodiazepin-6-one.

7. The method of claim 6 wherein $R_1$ is hydrogen and $R_2$ is methyl.

8. The method of claim 7 wherein the diazepinone is 5,11-dihydro-11-[1-oxo-2-methyl-6-(4-methyl-1-piperazinyl)-4-hexynyl)-6H-pyrido [2-3-b][1,4]benzodiazepin-6-one.

* * * * *